United States Patent [19]

Winnard

[11] 4,248,221
[45] Feb. 3, 1981

[54] ENDOBRONCHIAL TUBES

[75] Inventor: Ronald Winnard, Johannesburg, South Africa

[73] Assignee: Latex Products (Proprietary) Limited, Johannesburg, South Africa

[21] Appl. No.: 936,690

[22] Filed: Aug. 25, 1978

[30] Foreign Application Priority Data

Aug. 26, 1977 [ZA] South Africa .................... 77/5179

[51] Int. Cl.³ .................... A61M 25/00; A61M 16/00
[52] U.S. Cl. ........................ 128/207.15; 128/349 B
[58] Field of Search .......................... 128/348–351, 128/246, 207.15

[56] References Cited

U.S. PATENT DOCUMENTS

| | | | |
|---|---|---|---|
| 2,175,726 | 10/1939 | Gebauer | 128/349 B |
| 2,210,744 | 6/1940 | Winder | 128/349 B |
| 2,919,697 | 1/1960 | Kim | 128/349 B |
| 3,331,371 | 7/1967 | Rocchi et al. | 128/349 B |
| 3,392,722 | 7/1968 | Jorgensen | 128/350 R X |
| 3,395,710 | 8/1968 | Stratton et al. | 128/350 R |
| 3,417,744 | 12/1968 | Miskin et al. | 128/351 X |
| 4,140,119 | 2/1979 | Pollack | 128/214 R |
| 4,166,468 | 9/1979 | Haynie | 128/351 |

*Primary Examiner*—Dalton L. Truluck

[57] ABSTRACT

A single lumen endobronchial tube is provided which comprises a tube for location in the tracheo-bronchial tree of a patient. The tube has an endotracheal portion for location in the trachea and an endobronchial portion for location in one of the bronchi. The endobronchial portion communicates with the endotracheal portion, has an open end and a port spaced from the open end. Means such as inflatable cuffs are provided for locating the tube in position in a patient so that the open end of the endobronchial portion of the tube is in one bronchus while the port is in communication with the other bronchus. A further inflatable cuff is located in the lumen between the port and the open end to close off and isolate the endobronchial portion and that bronchus. The port remains in communication with the other bronchus whether or not the other bronchus is isolated.

7 Claims, 6 Drawing Figures

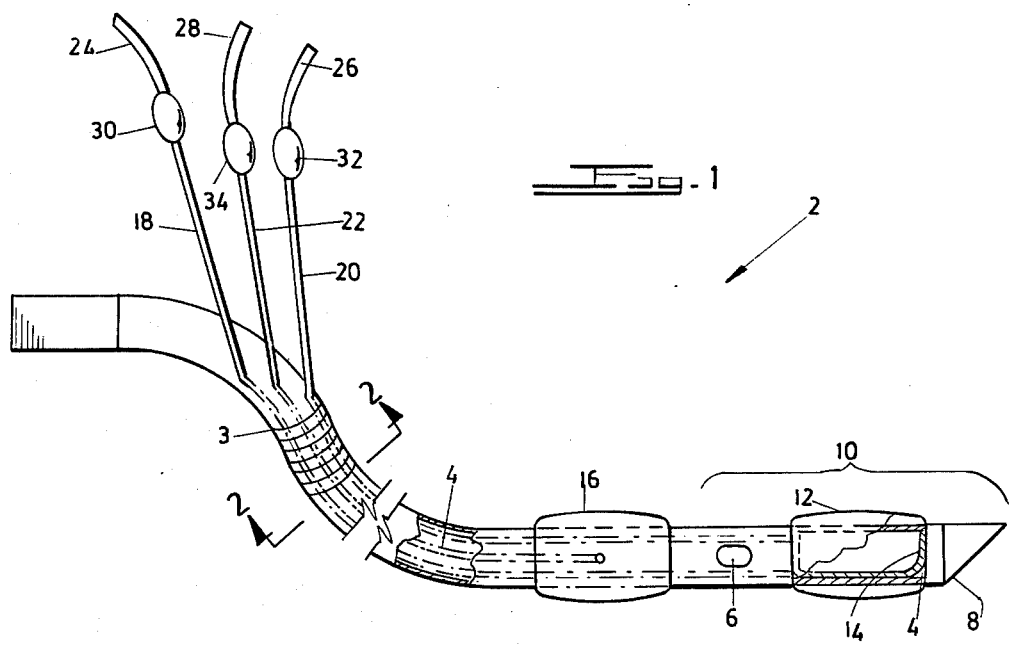
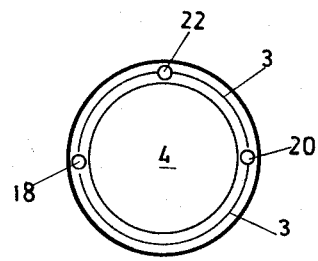
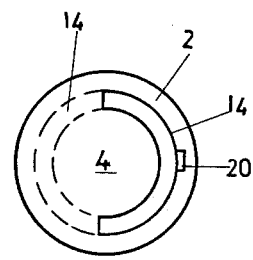

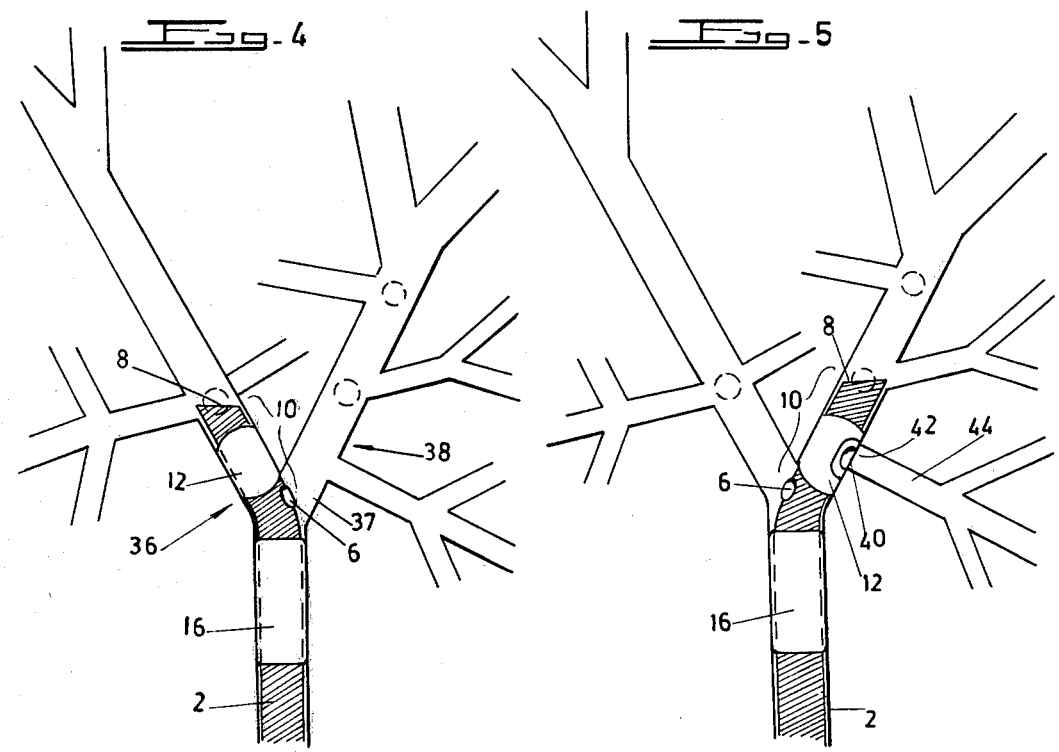
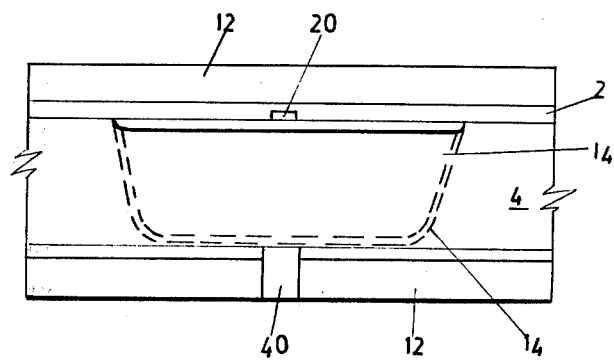

ENDOBRONCHIAL TUBES

BACKGROUND OF THE INVENTION

This invention relates to endobronchial tubes incorporating a novel blocking technique.

In thoracic surgery (for example in cases such as broncho-pleural fistulas and cysts of the lung) it is often necessary to isolate an infected lung while the other healthy lung is ventilated and operative. Secretions such as mucous or blood must be prevented from spreading across to the lung being operated on. The so-called "double-lumen" endobronchial tubes, such as the well known Carlens and the Robertshaw tubes, are commonly used for this purpose. These tubes allow independent control of each lung through the separate lumina. One lumen may be blocked off to isolate the infected lung, while anaesthetic gases may be fed along the other. These tubes take up valuable air space, and are for this and other reasons not fully satisfactory.

SUMMARY OF THE INVENTION

According to the present invention there is provided a single lumen endobronchial tube comprising:

an endotracheal portion communicating with an endobronchial portion which has an open end;

a port in the endobronchial portion spaced from the open end;

adjustable lumen-blocking means located between the port and the open end, the means being adjustable between a position wherein the lumen, and bronchus in which the endobronchial portion is placed, are blocked and a position wherein the lumen and bronchus are open; and means for anaesthesiologically placing the tube in the trachea and in one bronchus with the port communicating with the other bronchus.

This specific form of endobronchial tube of the invention will vary in form depending on whether it is intended for the left or the right lung. In the latter case allowance must be made for the upper lobe. If the endobronchial portion is of such a length that the free end of the tube lies beyond the entrance to the upper lobe, a tube for a right lung must include a further port so located that when the tube is in position it communicates with the entrance to the upper lobe, the lumen blocking means in this case being adapted to block the further port as well as the lumen.

DESCRIPTION OF THE DRAWINGS

In the attached drawings:

FIG. 1 illustrates a left-lung endobronchial tube of the invention;

FIG. 2 is a section along the line 2—2 of FIG. 1;

FIG. 3 illustrates diagrammatically, in cross-section, a lumen-blocking cuff;

FIGS. 4 and 5 illustrate the locations of left and right lung tubes, respectively, in a lung; and FIG. 6 illustrates diagrammatically a lumen-blocking cuff in a right-lung endobronchial tube.

DESCRIPTION OF THE PREFERRED EMBODIMENTS

According to a preferred form of the invention the lumen-blocking means comprises a balloon or inflatable cuff, remotely inflatable through a pilot tube, for example, by means of a syringe.

The balloon or cuff may be reinforced, for example with canvas.

The means for anaesthesiologically placing the tube in the bronchus and trachea may also be inflatable balloons or cuffs of a conventional type and inflatable through pilot tubes, for example, by means of a syringe.

The pilot tubes to the cuffs may in the conventional manner be provided with non-return valves, or may simply be clamped. They preferably also include the conventional pilot balloons to enable an anaesthetist to determine whether or not the cuffs have been inflated. The tube of the invention may be made from a soft natural or synthetic plastics material, preferably latex rubber, and may be reinforced, for example, by means of embedded filaments such as nylon. For example, the tubes may be simply formed by the well-known process involving dipping in liquid latex rubber.

Embodiments of the invention will now be described with reference to the accompanying drawings.

Referring to FIGS. 1 to 3 of the drawings, an endobronchial tube 2 formed from latex rubber and reinforced with nylon windings 3 has a single lumen 4, and is formed with a port 6 spaced from its open endobronchial end 8. The portion 10 between and including the open end 8 and port 6 comprises the endobronchial portion of the tube 2. An external inflatable cuff 12 of the type well-known in conventional endobronchial tubes or catheters is provided between the open end 8 and the port 6. By means of this cuff 12 the endobronchial portion 10 may be placed anaesthesiologically in the left bronchus of a lung (for reasons discussed below, a slight modification is necessary in the case of a right-lung tube). A further balloon or cuff 14 is provided in the lumen 4 in this endobronchial portion 10, and when inflated as shown in FIG. 1, blocks the lumen 4. The operation of the cuff 14 is shown diagrammatically in FIG. 3 wherein the solid line illustrates the cuff 14 in its collapsed state, while the dotted line illustrates the cuff 14 in its expanded lumen-blocking state.

The tube 2 also includes an external inflatable cuff 16 on its endotrachael portion for anaesthesiologically placing this portion in the trachea. The three cuffs 12, 14 and 16 are all remotely inflatable through conventional pilot tubes 18, 20 and 22 respectively, located in the tube 2 as illustrated particularly by FIG. 2. The pilot tubes incorporate non-return valves illustrated diagrammatically at 24, 26 and 28, each adapted to receive the nozzle of a syringe, and pilot balloons 30, 32 and 34 which enable an anaesthetist to confirm that each cuff 12, 14 and 16 has been inflated. These features are standard and well known in the art, and no further explanation is necessary.

In use, as shown in FIG. 4, the endobronchial portion 10 of the tube 2 is inserted into the left bronchus 36 of a lung, with the port 6 communicating with the entrance 37 to the right bronchus 38. The bronchial cuff 12 and tracheal cuff 16 are inflated to place the tube 2 anaesthesiologically, and the left lung is blocked off by inflating the cuff 14 in the lumen 4. Anaesthetic gases may be fed to the right lung through the tube 2 and port 6.

FIG. 5 is similar to FIG. 4 except that it illustrates a right-lung tube, and corresponding components of the tubes illustrated therein are numbered similarly. The right-lung includes an upper lobe, which, if the left-lung tube 2 were employed as it would be blocked off. Accordingly, for use in the right-lung the endobronchial portion is modified. Referring to FIG. 5, an endobronchial tube 2 has an endobronchial portion 10 similar to the endobronchial portion 10 of the tube 2 of FIGS. 1 to 3 except that there is a further port 40 which, when the endobronchial portion 10 is in position, communicates with the entrance 42 to the upper lobe 44. The port 40 extends through the outer cuff 12. When the inner cuff 14 is inflated the port 40 is blocked. This is illustrated diagrammatically in FIG. 6, where the solid lines illustrate the cuff 14 in its collapsed position and the dotted lines illustrate the cuff 14 in its inflated position.

The endobronchial tubes 2 of the invention have a number of important advantages. Because they are formed with a single, wide diameter circular lumen, they exhibit a much lower resistance to gas-flows than do conventional double lumen tubes. Further, the lumen-blocking cuffs 14 may be deflated very rapidly, substantially instantaneously, to allow rapid access to the isolated lung in the case of an emergency or for reflation. Further, the tubes 2 may be formed from a soft pliable material such as latex rubber with relatively thin walls, and accordingly are relatively easily inserted into the trachea and bronchi. A further very important advantage is that because of their relatively low resistance to gas-flows, they are suitable for child-patients, for their diameters may be decreased to child-sizes while maintaining a relatively low gas-flow resistance.

The invention is of course not limited to tubes of the type specifically described above, but extends to all endobronchial tubes which incorporate means for blocking or obstructing the lumen, which blocking means preferably comprises an inflatable cuff or balloon of the type described herein.

I claim:

1. A flexible single lumen endobronchial tube having an annular tube wall and comprising:
   an endotrachial tube portion;
   an endobronchial tube portion sized for placement in one of the bronchi, said endobronchial portion directly communicating with and being an integral extension of said endotrachial portion and having an open end;
   first expansible means on the outer surface of said tube for anaesthesiologically sealing the tube in the trachea;
   second expansible means spaced from said first means on the outer surface of the tube for anaesthesiologically sealing the tube in one bronchus so that said open end opens into said one bronchus;
   port means formed in the tube wall of said endobronchial portion between said first and second expansible means to communicate with the other bronchus; and
   adjustable lumen-blocking means located in the lumen between the port and the open end, and being adjustable between a position in which the lumen and the bronchus in which the said endobronchial portion is located is blocked and a position in which said lumen and bronchus are open, said port being in communication with the other bronchus in both positions of said adjustable means.

2. An endobronchial tube according to claim 1 wherein the adjustable lumen-blocking means comprises an inflatable cuff remotely inflatable through a pilot tube.

3. An endobronchial tube according to claim 2 wherein the cuff consists of a flexible membrane secured at its edges to the inside of the tube and in communication with the pilot tube.

4. An endobronchial tube according to claim 1 which is made from a soft natural or synthetic plastic material.

5. An endobronchial tube according to claim 4 which is made of latex rubber.

6. An endobronchial tube according to claim 5 which is reinforced by means of embedded filaments.

7. An endobronchial tube according to claim 6 wherein the filaments are nylon.

* * * * *